United States Patent
Hopkins et al.

(10) Patent No.: US 12,268,852 B2
(45) Date of Patent: Apr. 8, 2025

(54) MULTI-SENSORY FEEDBACK INJECTION TRAINING DEVICE

(71) Applicant: NOBLE INTERNATIONAL, LLC, Orlando, FL (US)

(72) Inventors: Joshua Hopkins, Casselberry, FL (US); Tingting Liu, Orlando, FL (US); Shishuang Hou, Ningbo (CN)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 1205 days.

(21) Appl. No.: 17/076,447

(22) Filed: Oct. 21, 2020

(65) Prior Publication Data

US 2021/0113776 A1    Apr. 22, 2021

Related U.S. Application Data

(60) Provisional application No. 62/923,950, filed on Oct. 21, 2019.

(51) Int. Cl.
    G09B 23/28      (2006.01)
    A61M 5/142     (2006.01)
    A61M 5/315     (2006.01)
    A61M 5/32      (2006.01)

(52) U.S. Cl.
    CPC .... A61M 5/31543 (2013.01); A61M 5/31511 (2013.01); A61M 5/31581 (2013.01); A61M 5/3202 (2013.01); G09B 23/285 (2013.01); A61M 2005/14288 (2013.01); A61M 2205/582 (2013.01); A61M 2205/583 (2013.01)

(58) Field of Classification Search
    CPC ...... G09B 23/28; G09B 23/285; A61M 5/142; A61M 2005/14288
    See application file for complete search history.

(56) References Cited

U.S. PATENT DOCUMENTS

| | | | |
|---|---|---|---|
| 2013/0236872 A1* | 9/2013 | Laurusonis | G09B 23/285 434/262 |
| 2017/0148354 A1* | 5/2017 | Baker | A61M 5/326 |
| 2017/0337844 A1* | 11/2017 | Baker | G09B 19/24 |
| 2020/0265753 A1* | 8/2020 | Baker | G09B 23/285 |
| 2021/0268198 A1* | 9/2021 | Baker | A61M 5/31543 |
| 2022/0208024 A1* | 6/2022 | Chao | A61M 5/178 |

OTHER PUBLICATIONS

BD Intevia™ Handheld Autoinjector, Dowloaded on May 17, 2021, https://drugdeliverysystems.bd.com/products-and-services/products/self-injection-systems/intevia-handheld-autoinjector, 5 pages.

Self-Injection Systems—BD, Downloaded on May 17, 2021, https://drugdeliverysystems.bd.com/products-and-services/products/self-injection-systems, 10 pages.

* cited by examiner

*Primary Examiner* — Jay Trent Liddle
*Assistant Examiner* — Alyssa N Brandley
(74) *Attorney, Agent, or Firm* — Timothy H. Van Dyke; Wolter Van Dyke Davis, PLLC

(57) ABSTRACT

In embodiments herein, a resettable injection training device is provided including an outer housing, an inner housing, said inner housing moving relative to the outer housing during actuation and reset, a tactile feedback indicator and/or a visual feedback indicator, wherein actuation of the device delivers a tactile and/or visual feedback; and a reset cap for resetting the device to a reset position, such that the reset cap resets the tactile and or feedback indicator to a pre-use position, for a subsequent use.

21 Claims, 11 Drawing Sheets

MULTI-SENSORY FEEDBACK INJECTION TRAINING DEVICE

BACKGROUND

Injection devices have recently become increasingly popular for single dose or multi-dose, at home self-administration. These devices include both auto-injection devices and pre-filled syringe devices and are often designed to accomplish two basic objectives: convenience of drug delivery in an outpatient or at home setting, and/or automation of drug delivery in an outpatient or at-home setting.

Injectable medications are required for a number of varying illnesses and diseases. A number of injectable medications require self-injection by a patient. Self-injection of a medicament using a device having a needle carries with it a certain stigma. Oftentimes patients are weary of injecting themselves for fear or anxiety related to failing to receive a complete dose of the medication, pain associated with injecting oneself with the needle, accidentally sticking oneself with the needle, and difficulties in adequately grasping the dosing mechanism to inject oneself, among other concerns. These fears and anxieties associated with the currently available self-injection devices may result in the administration of an incomplete dose of a medicament, failure to administer any portion of the dose of a medicament, or accidentally sticking oneself with the needle of the device, which in some instances could lead to unwanted transmission of diseases if the needle is contaminated.

An additional concern exists with respect to injection devices involving users with little or no medical knowledge or experience who are injecting themselves or injecting others using these devices. Performing a medical treatment or test on oneself or others carries certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self-administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices to assist in training individuals to inject themselves or otherwise self-administer medication are beneficial in decreasing or preventing the anxiety associated with medicament delivery. Safe use and re-use of these training devices requires a resettable device. Therefore, a device which allows repeated practice and ease of use to enhance familiarity with the injection device and the self-injection process, along with the ability to safely and efficiently reset the device is paramount to an effective device for injection training.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1A:
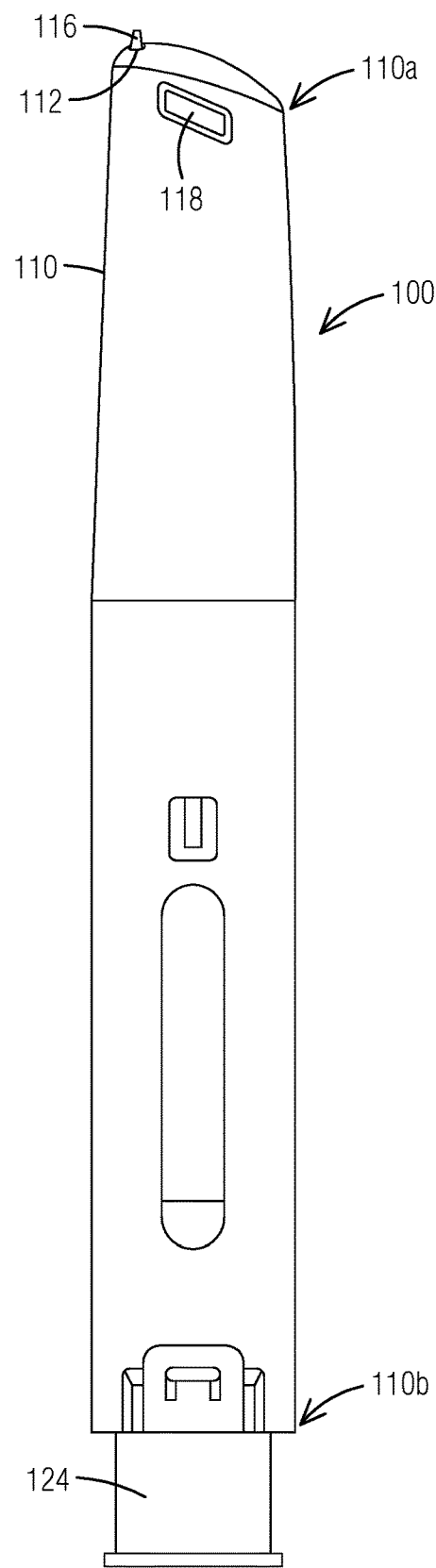
FIG. 1A is a side view of a resettable injection training device embodiment.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

The term associated or association, as used herein, includes but is not limited to direct and indirect attachment, adjacent to, in contact with, partially or fully attached to, and/or in close proximity therewith. The term "in conjunction with" as used herein includes but is not limited to synchronously or near synchronous timing, the phrase may also include the timing of outputs, where one output directly follows another output.

As used herein, the terms "subject", "user" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

Multi-Sensory Feedback

In addition to increasing confidence in self-administration in users by practicing with a injection training device, additional benefits associated with multi-sensory learning regarding a injection training device have been identified herein. It has been discovered that multi-sensory learning establishes multiple pathways in separate areas in the brain and ultimately results in a highly effective learning experience. However, in order to gain benefits from multi-sensory learning devices, certain requirements must be met including but not limited to the following: the sources of stimuli must be in close proximity to one another; the sources of stimuli must be synchronous; the stimuli must be congruous semantically, otherwise the superior colliculus (area of the brain located in the midbrain known for integrating multiple sources of information) will segregate the stimuli instead of integrating them; and finally, the use of extraneous materials should be limited.

With knowledge of the essential factors in multi-sensory learning and incorporation of the multi-sensory learning features into a training system, the inventors have developed a novel, cutting-edge injection training device. The inventors have identified a need for a system to provide users with a training device for medication administration including one or more modes of feedback to assist in the training process.

Embodiments of the system described in greater detail below include applications for home use, in-office use by health care provider (HCP) or by the patient, hospital use, and educational use for training medical professionals and other personnel among other potential uses. The inventors have discovered a system for training individuals to use medical devices while improving user comfort and confidence in delivery and administration of medicament, using multi-sensory feedback.

In addition to increasing confidence in self-administration in users by practicing or training with an injection training device, the inventors have identified additional benefits associated with multi-sensory learning with an injection training device.

The injection training device takes advantage of the multisensory learning capabilities of the human brain. As such, the injection training device provides the means to stimulate primarily the visual, auditory and somatic systems of the human nervous system.

Visual stimuli or feedback (visual output) can be generated mechanically or electronically. An example of a mechanically generated visual stimulus is a plunger moving past an inspection window in an autoinjector or prefilled syringe medicament device or a shroud extending from an injection device. An example of an electronically generated visual stimulus is one or more LED's blinking, an LCD display showing an icon, or key steps in the process of administration being highlighted on a screen in the order required for proper administration of medicament, in non-limiting examples. Other examples may include movement of one or more elements of the device relative to one another to indicate status of the device during use thereof. For example, as described above, mechanical visual output can be generated by movement of a visible plunger traversing an inspection window. In another example described in more detail below, movement of another component of the device, such as for example, a protrusion which may be in a first position (which in some instances may not be visible to the user) during one state of the injection device, and may be in a second position wherein, in one non-limiting example, it may extend from the device such that it may provide both a visible and tactile feedback to the user to indicate the status or state of the device to the user. A visual output as disclosed herein includes but is not limited to a light, a display, a colorimetric display system, a change in position of the device or a component thereof, or extension or retraction of a device component, for example, or any other type of visual cue to the user of the container and/or device. The visual output is associated with the medicament device or with the medicament training container; therefore, it may be disposed on either portion of the device or provided in connection with the device either by a wire or wirelessly.

Additional visual outputs that may be incorporated into the system herein may include display devices having one or more layers of material having a light transmission region, a unit of information to be highlighted, and a light blocking region; and a backlight unit having a flexible, planar waveguide body, a light source configured to direct light into the waveguide body, and at least one light director associated with a portion of the waveguide body so as to direct light transversely to a plane of the waveguide body. The directed light travels through the light transmission region, and the directed light is directed toward the unit of information to be highlighted as provided in International Application No. PCT/US11/26976 and US National Stage application Ser. No. 13/582,560 which claim the benefit of U.S. Provisional Application Ser. No. 61/310,081, which are incorporated by reference in their entireties herein. The unit or units of information to be highlighted may include the stepwise instructions for administering the medicament to a user and may also provide the duration of each step by way of highlighting each step for a predetermined amount of time such that the user can follow the precise timing of each step in the sequence.

Auditory stimuli or feedback (audio output) can also be generated mechanically or electronically. An example of a mechanically generated auditory stimulus is the "click" that can be heard if two parts of a device interlock. An example of an electronically generated auditory stimulus is a beeper or a speaker that plays spoken instructions. An audio output as disclosed herein can be generated mechanically or electronically, for example, and includes but is not limited to music, a sound, a beep, a series of beeps music or sounds, a mechanical sound including clicking, the movement of one or more parts of a medicament device relative to one another, or a sound replication of operation or behavior of a drug delivery device containing medicament. These auditory stimuli, such as two parts of a device interlocking can be picked up by a microphone of the system. The microphone may be associated with the collateral device in a non-limiting example and may receive audio input from the medicament device as described above during use of the system. The device may then identify whether or not the device was used correctly (i.e., whether a step was performed correctly or in the correct order, for example). A combination of both visual and auditory output may include a video tutorial providing instructions to a user on proper administration of the medicament or use of the training device, for example.

Somatic stimuli or feedback, also called somatosensory stimuli or tactile feedback, is typically generated mechanically. In a typical embodiment of the injection training device, there are a large number of somatic stimuli, particularly with reference to the medicament device, such as actuation forces, abrasion resistance, frictional forces, spring compression, the feel of a click if two parts interlocking, surface texture, vibrations, weight sensation, and any other similar stimuli or feedback known to those of skill in the art. As aforementioned, various mechanical components of the device may provide tactile feedback, for example, such as movement of one component of the device relative to another, or extrusion or retraction of a component of the device, in non-limiting examples.

Another important feature of an injection training device includes reset-ability. A training device must be resettable such that a user may continue to train with the device to achieve a level of comfort translating to a level of accuracy when using the medicament delivery device. Resetting an injection training device requires interactivity of multiple components of the device in order to achieve a pre-use (i.e. reset) position or state to ensure repeatability of the injection training. Consequently, in one example, an injection training device for simulating an injection with a medicament delivery device is provided herein. The device includes feedback for a user to indicate the status of the device, before, after, or during use thereof, and the training, as well as a method for resetting the device for a subsequent use to facilitate repeatability of training. Repeatable training enhances confidence of a user during an injection with a medicament delivery device, and increases and maintains accuracy during use of a medicament delivery device.

Figure 1B:
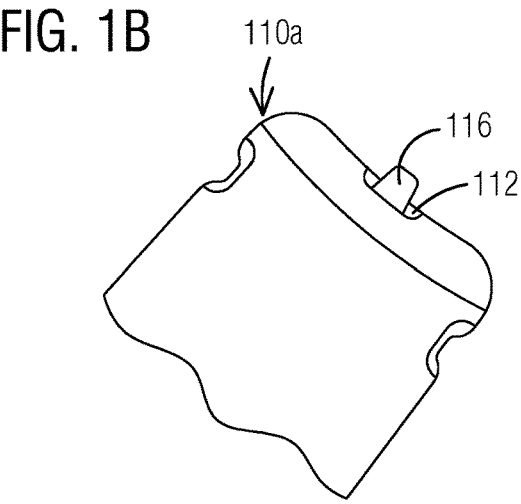
FIG. 1B is a partial side view of a resettable injection training device embodiment.
Figure 1C:
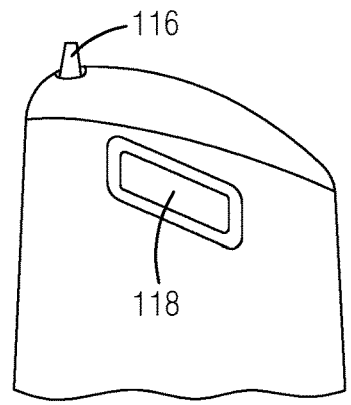
FIG. 1C is a partial side view of a resettable injection training device embodiment.
Figure 1D:
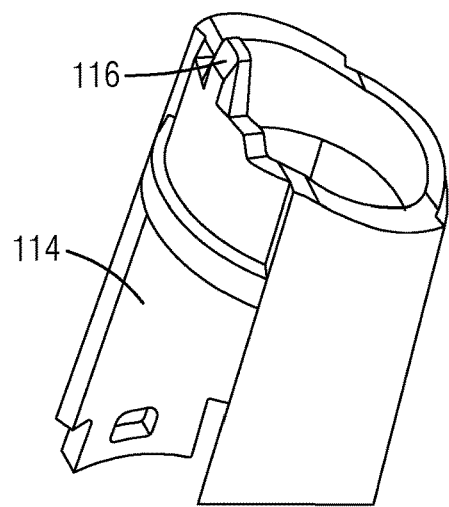
FIG. 1D is a partial view of an inner housing of a resettable injection training device embodiment.

Turning to the drawings, FIG. 1A provides a side view of a resettable injection training device according to an embodiment. In the embodiment 100 shown in FIG. 1A, the device comprises an outer housing 110 comprising an outer housing proximal end 110a and a distal end 110b. The outer housing comprising an aperture 112 for receiving a protrusion 116 in one embodiment to provide tactile feedback during use of the device 100. The outer housing 110, in one embodiment may also include an indicator window 118 to provide visual and/or tactile feedback to a user of the device during use of the device 100. The indicator window 118 may provide an indication of the state of the device, whether pre-use, reset, during use, or otherwise, to a user. The device may include an inner housing 114 (shown in FIG. 1D), wherein the inner housing 114 moves relative to the outer housing 110 during actuation of the device and during reset thereof. The outer housing 110 may include an aperture 112 (shown at the proximal end in FIG. 1B). The inner housing 114 may move proximally relative to the outer housing 110 during actuation until a protrusion 116 of the inner housing extends through or into the outer housing 110. In one example, the protrusion 116 may traverse the outer housing 110 as shown in FIG. 1A-1C via the aperture 112 in the outer housing to indicate completion of an injection simulation. The device may therefore provide a non-visual, tactile feedback to a user that a simulation has been completed, wherein a user can physically feel the protrusion extending through the outer housing indicating a change in state. In one non-limiting example, that state is completion of the injection training. Alternatively, or in addition, an indicator window 118 in the outer housing may display visual feedback that an injection simulation has, or has not been completed. In one example, as shown in FIGS. 1A, 1C, movement of the inner housing in a proximal direction relative to the outer housing 110 during use of the device results in a visual indication of simulation wherein the inner housing 114 is viewable via the indicator window 118 in the outer housing once injection simulation is complete. Multiple sensory outputs may occur to establish multiple pathways in the brain and further enhance the training experience.

Extending from the distal end of the outer housing 110b in FIG. 1A is a safety shield 124. The safety shield 124 may include an extended unlocked position prior to use, and following reset of the device, in non-limiting examples (as shown in FIG. 1A). The safety shield may also include a retracted position, wherein a force on the end of the safety shield 124 (i.e., when the safety shield is pressed against a target surface, the safety shield 124 may be moved toward the proximal end to a retracted position, for example) causes the safety shield to retract into the outer housing 110. Retraction of the safety shield 124 in this manner may initiate actuation of the device 100, in one non-limiting embodiment. Other methods of actuation may include by compressing a button, or by both compressing a button and activating the safety shield in other examples. These components may further contribute to the multi-sensory feedback, including visual, audible and tactile feedback.

Figure 2A:
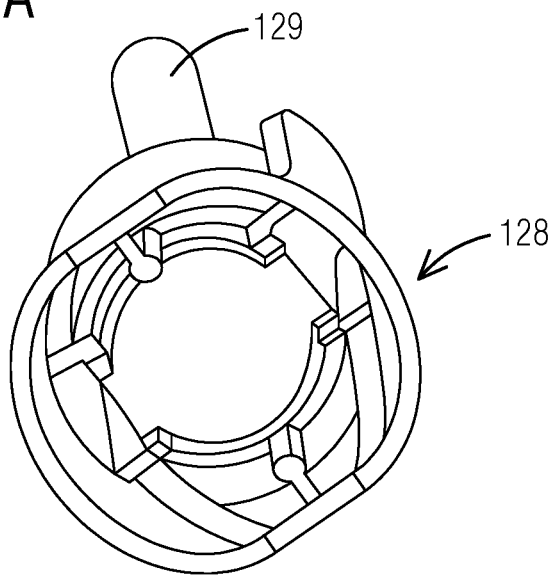
FIG. 2A is a bottom view of a reset cap embodiment.
Figure 2B:
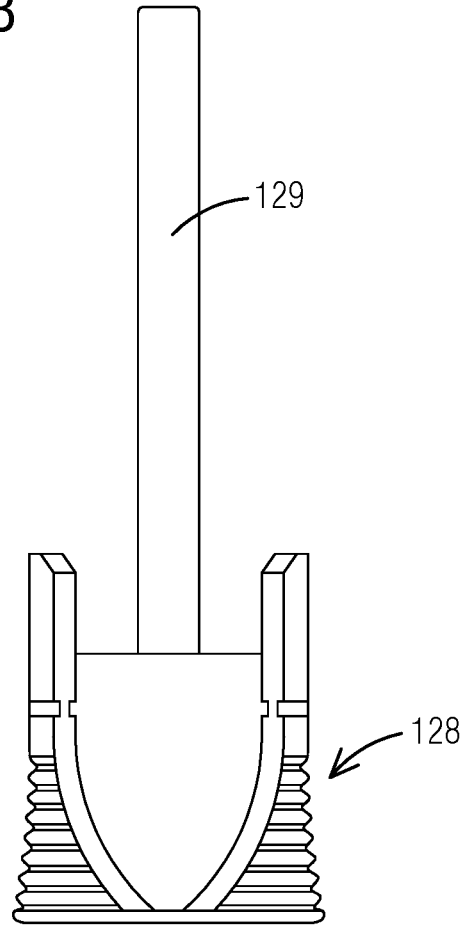
FIG. 2B is a side view of the reset cap embodiment shown in FIG. 2A.

The safety shield 124 may also include an extended, locked position. The safety shield 124 may take the extended locked position following use of the device 100 (i.e., after completion of an injection simulation, for example) and until the device is reset for a subsequent use. In order to reset the device, a reset cap 128 as shown in FIGS. 2A-2B may be used. The reset cap 128 may be removed from the distal end of the device 100 prior to use of the device 100 in one embodiment. Consequently, the same reset cap 128 may be used to reset the device 100 following use of the device 100. In order to reset the device 100 using the reset cap 128, the elongated rod 129 is inserted into the distal end of the device 100, and the cap 129 is moved in a proximal direction relative to the device (i.e., the elongate rod 129 is moved into the device 100). The reset cap 128 resets the device as will be explained in detail below.

An optional opening in the outer housing may also be included to provide a user with an indication of the status of an injection. In one embodiment, the plunger may be viewable via the opening in the outer housing 110, providing a visual indication of whether the plunger has reached its final destination during a simulated injection (i.e., if the plunger has moved to its most distal position within the housing).

Figure 3:
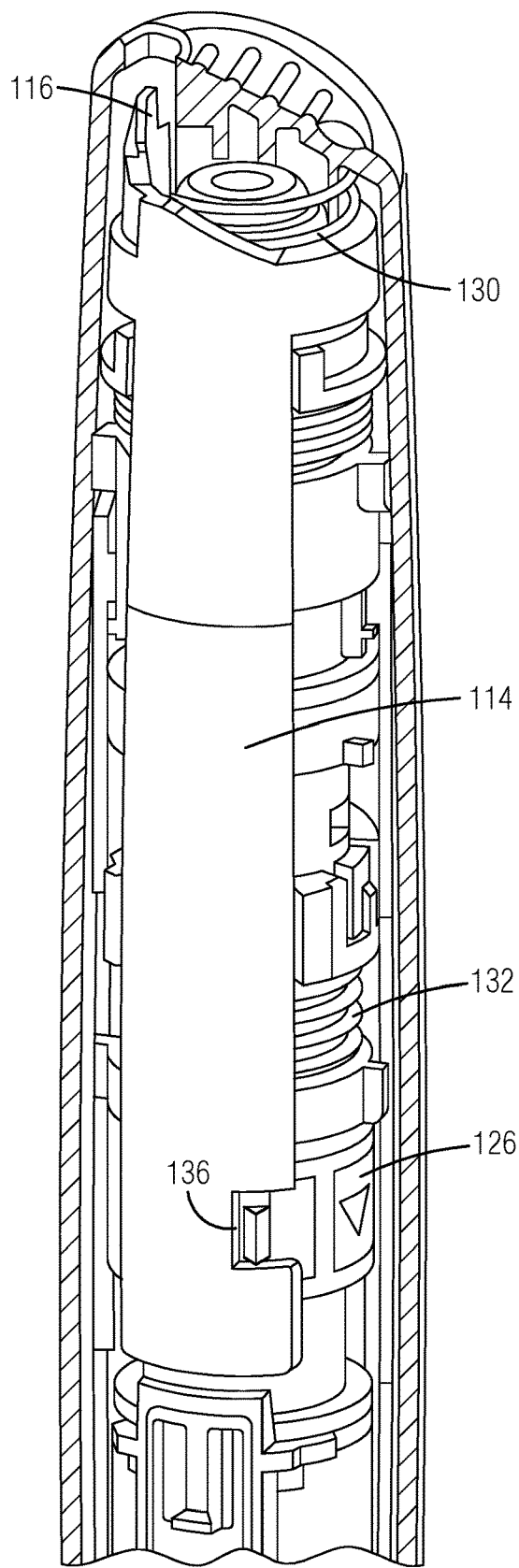
FIG. 3 is a partial sectional view of the resettable injection training device embodiment of FIG. 1 prior to injection simulation.

FIG. 3 provides a partial sectional view of the device 100, wherein a portion of the outer housing 110 has been cut away to expose the inner housing 114. The inner housing 114 is shown with the protrusion 116 extending from its proximal end. The inner housing 114 is maintained in a pre-actuation position by interfacing with a rotating member 126. The rotating member 126 includes (as shown in detail in FIG. 5B) an outer tab 134 and an inner tab 138. The outer tab interfaces with a groove 136 in the inner housing to keep the inner housing toward the distal end of the device prior to actuation of the device 100. FIG. 3 also provides a view of the first spring 130 (also referred to as the indicator spring or inner housing spring) and a second spring 132 (also referred to as the actuation member spring or rotating member spring). The first and second springs 130, 132 may include compression springs in a non-limiting embodiment. Other types of springs known to those skilled in the art may be used in the device 100.

Figure 4A:
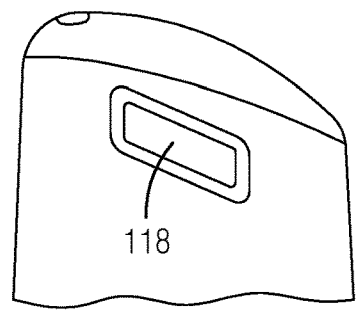
FIG. 4A is a side view of a portion of the resettable injection training device embodiment shown in FIG. 4.
Figure 4B:
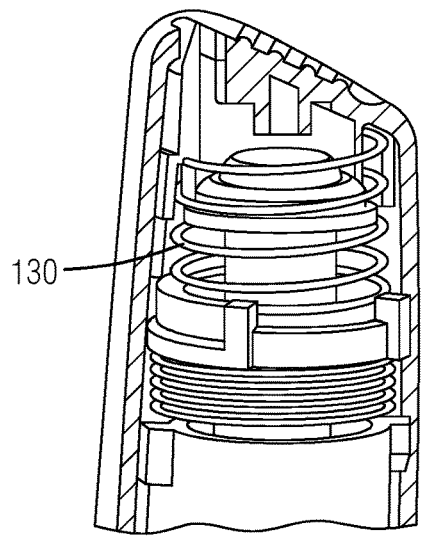
FIG. 4B is a sectional view of the portion of the resettable injection training device embodiment shown in FIG. 4A.

FIGS. 4A-4B provide side and partial sectional views of the proximal end of the device 100. FIG. 4A provides a view of the indicator window 118 indicating actuation of the device 100 has not occurred. FIG. 4B demonstrates the view inside the device 100 when the device is in the state shown in FIG. 4A prior to actuation of the device. The first spring 130 is viewable in FIG. 4B.

Figure 5A:
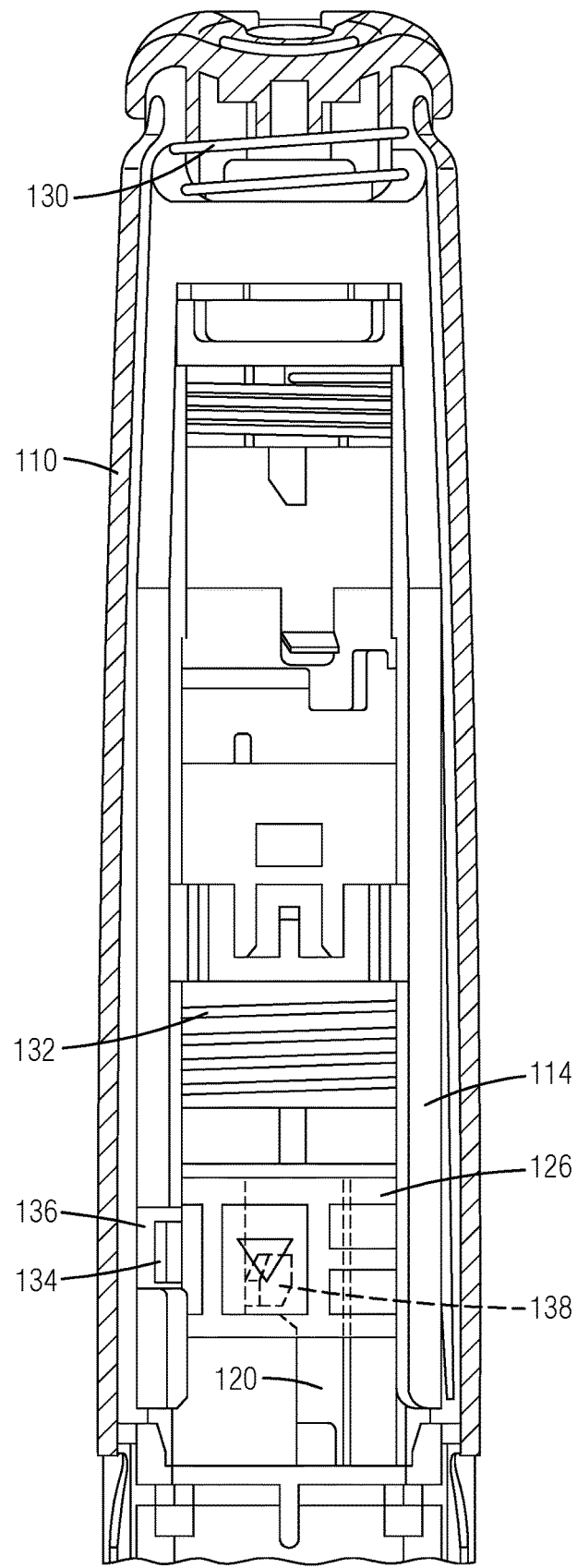
FIG. 5A is a partial sectional view of the resettable injection training device embodiment of FIG. 1 prior to injection simulation.
Figure 5B:
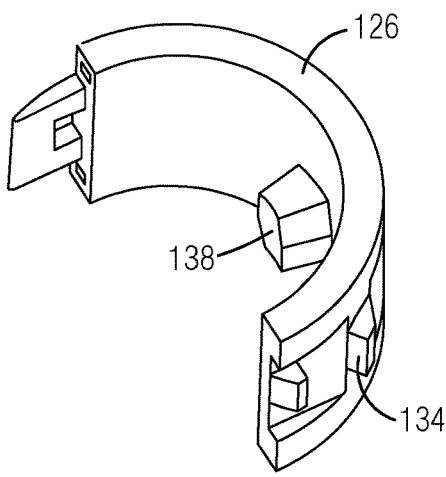
FIG. 5B is a perspective view of a portion of an embodiment of a rotating member.

FIG. 5A shows a partial sectional view of the device 100 with outer housing partially removed to reveal the inner structures of the device embodiment. Inner housing 114 is shown, and second spring 132 in contact with rotating member 126 is also shown. FIG. 5B provides a partial view of the rotating member 126, providing a view of the inner tab 138 and outer tab 134. In other embodiments, the rotating member 126 may have multiple inner and outer tabs 138, 134. The rotating member 126 is also provided in FIG. 5A; however it is shown as translucent such that the viewer can see the components of the rotating member 126, such as the inner tab 138. The second spring 132 is associated with the rotating member 126. The plunger 120 can also be seen in FIG. 5A. Prior to initiation of an injection simulation, the rotating member 126 and the inner housing are axially engaged by virtue of interface between the rotating member outer tab 134 and an inner housing groove 136 as seen in FIGS. 3 and 5A.

Figure 6:
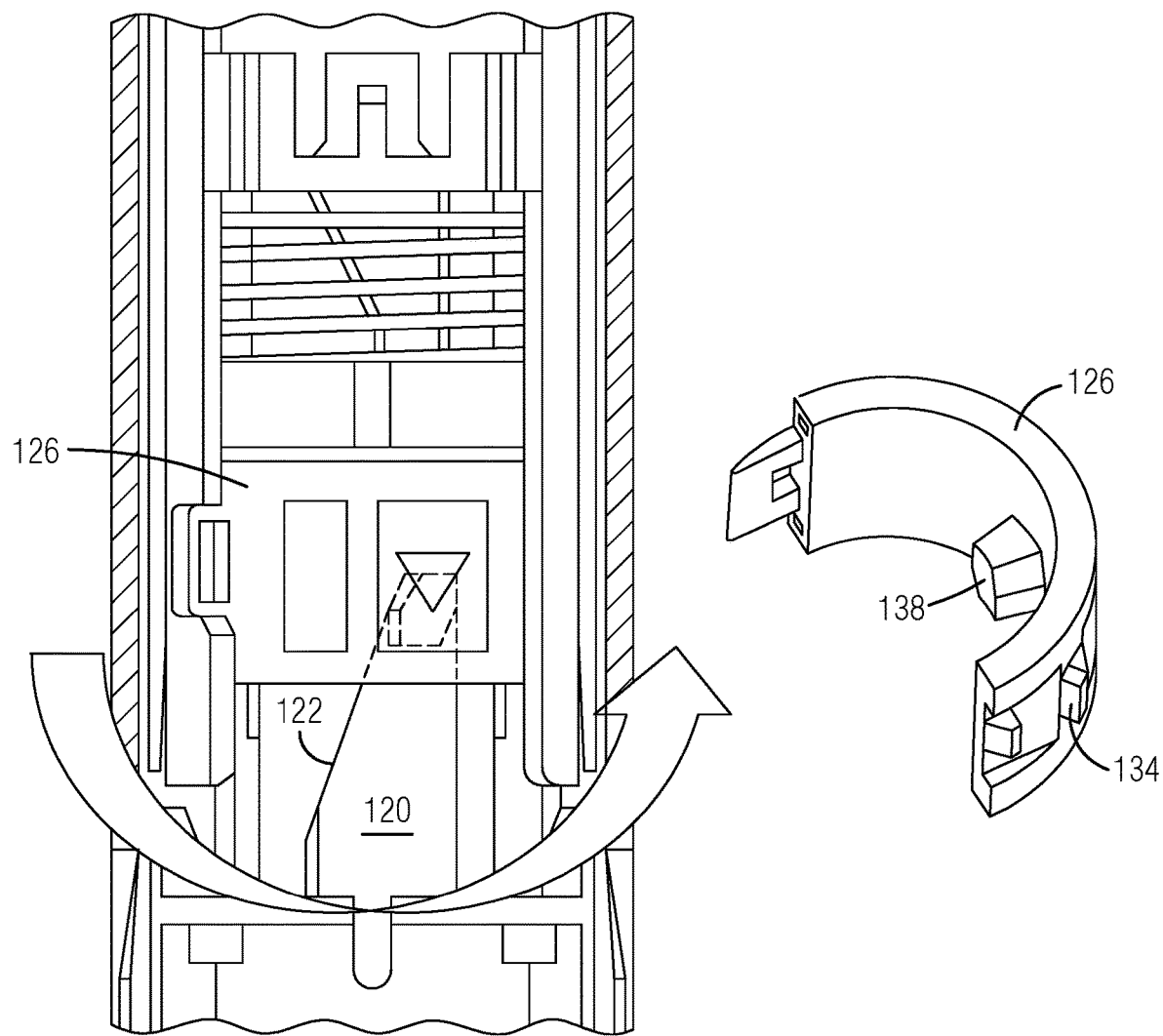
FIG. 6 is a partial sectional view of a resettable injection training device embodiment during use.
Figure 7:
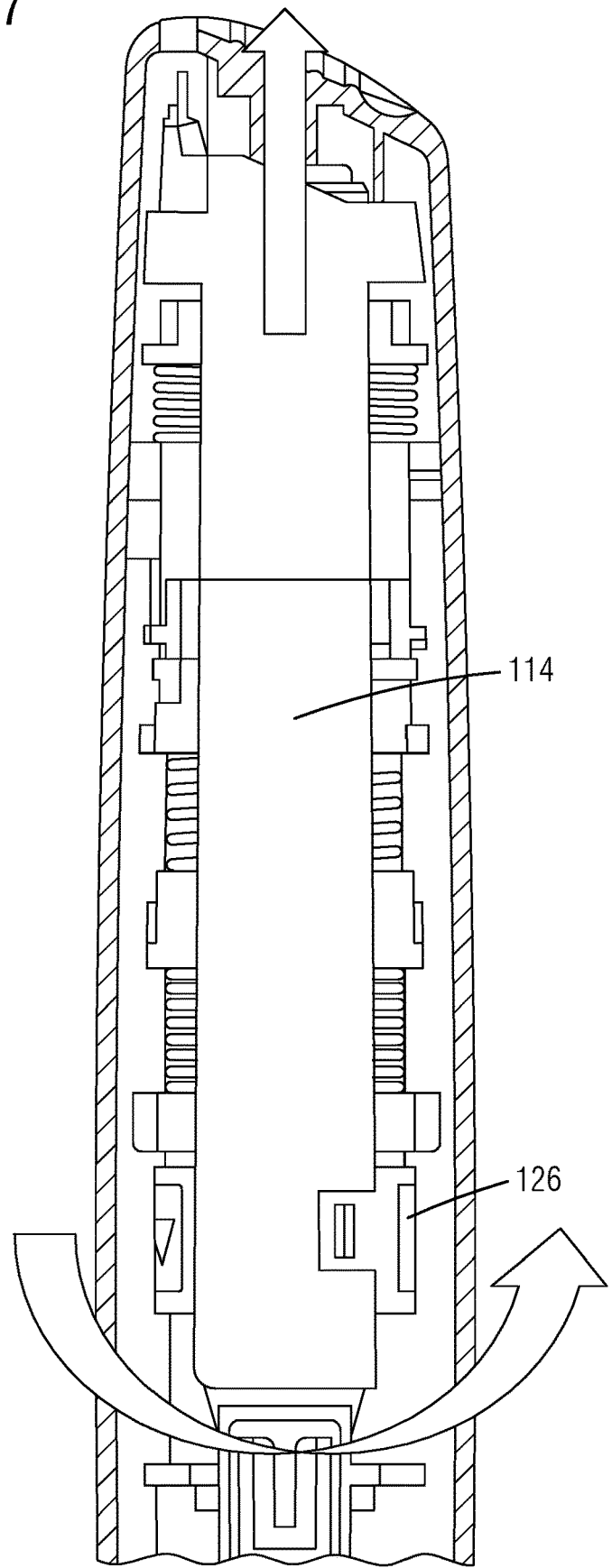
FIG. 7 is a partial sectional view of a resettable injection training device embodiment during use.
Figure 8A:
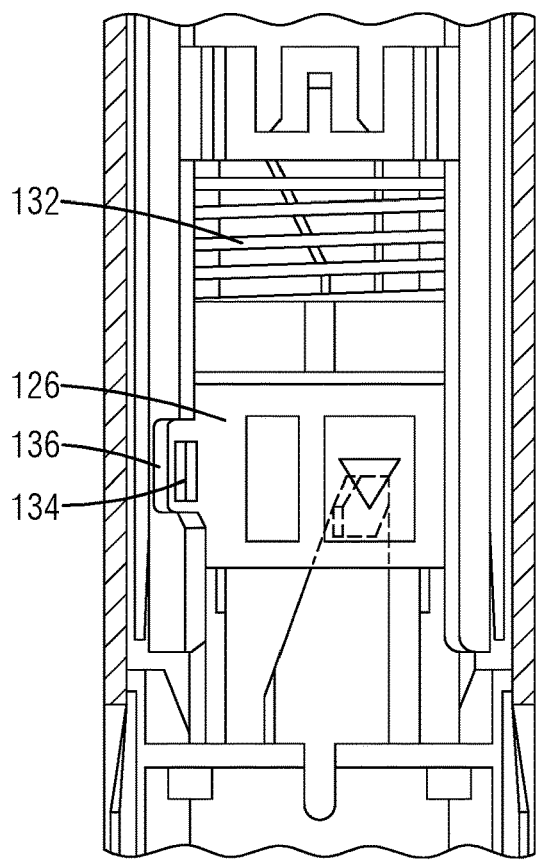
FIG. 8A is a partial sectional view of a resettable injection training device embodiment during use.
Figure 8B:
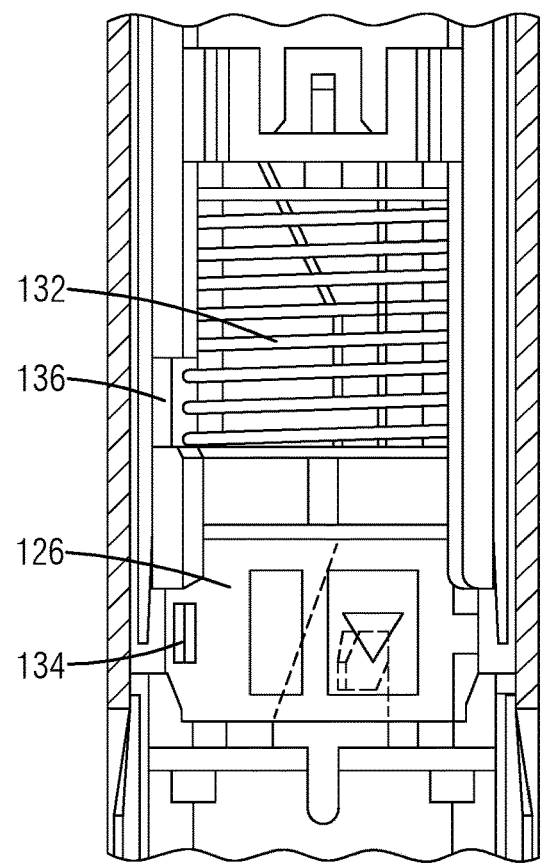
FIG. 8B is partial sectional view of a resettable injection training device embodiment during use.

Upon actuation of the device 100 (i.e., by a force on the safety shield, for example), the plunger 120 moves distally within the device. Actuation of the device by moving the safety shield from an extended, unlocked position to a retracted position may provide a first audible signal, in one non-limiting embodiment, indicating initiation of injection simulation. A plunger ramp 122 (shown in FIG. 6) interfaces with the rotating member 126, moving the rotating member in a first direction as shown by the arrow in FIG. 6, for example. The ramp 122 interfaces with the inner tab 138 of the rotating member. This rotation of the rotating member 126 releases the outer tab 134 from the groove of the inner housing 136, allowing the inner housing to move in a proximal direction relative to the device 100. In one embodiment, the first spring 130 forces the inner housing 114 toward the proximal end of the device 100 as shown in FIG. 7. Release of the outer tab 134 from the inner housing groove 136 also allows the rotating member 126 to move toward the distal end of the device 100, in one embodiment, under the force of the second spring 132 as shown in FIGS. 8A-8B. As second spring 132 extends, the rotating member 126 moves distally within the device 100. Completion of distal movement of the rotating member 126 is marked by a second audible click, in some embodiments, to signal completion of a simulation.

Figure 9A:
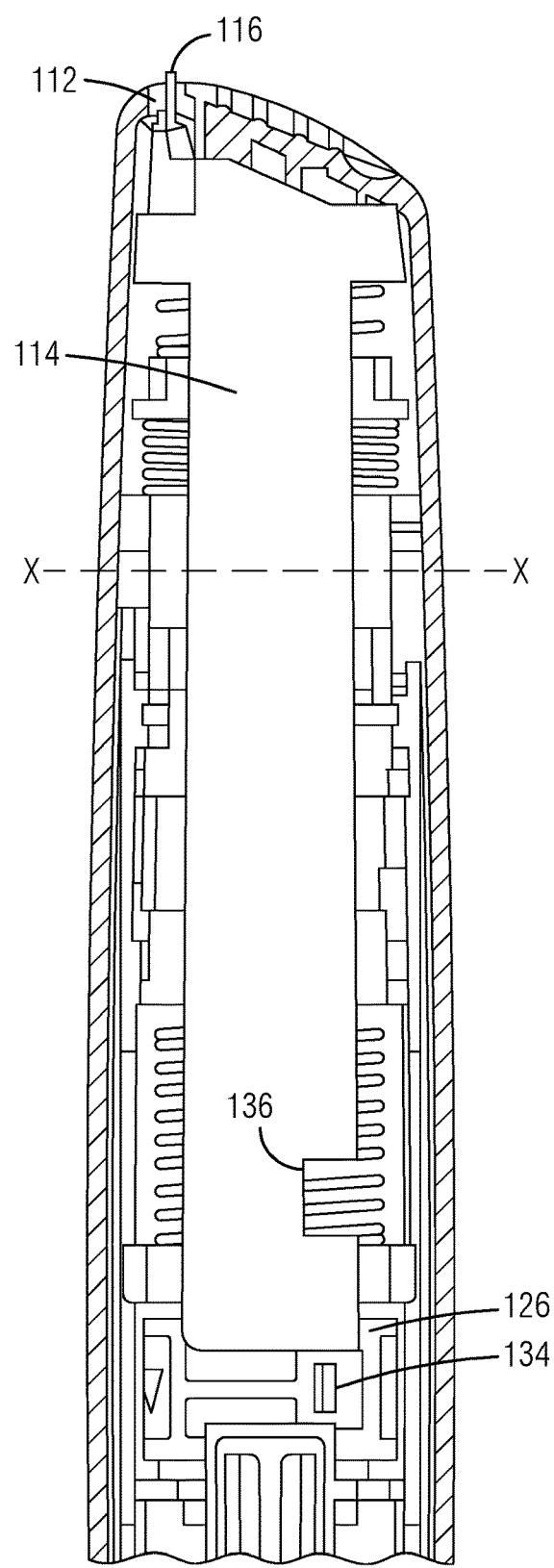
FIG. 9A is a partial sectional view of a resettable injection training device embodiment during use following actuation.
Figure 9B:
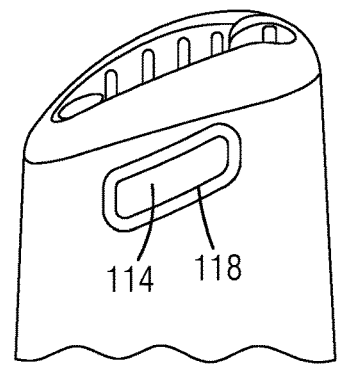
FIGS. 9B-9D are side and partial sectional views of a proximal end of the device shown in FIG. 9A.
Figure 9C:
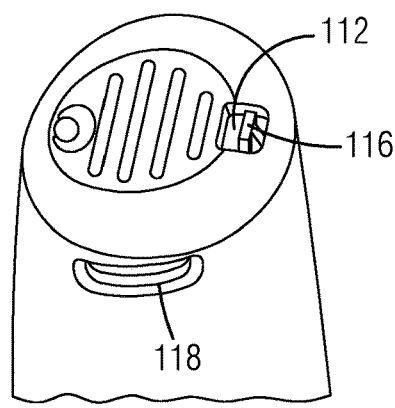
Figure 9D:
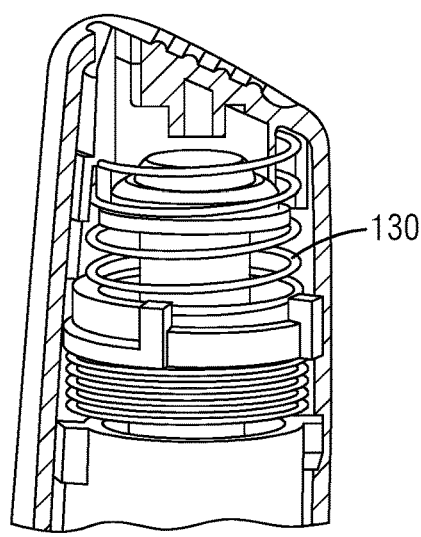

Once the inner housing 114 reaches its most proximal position following completion of the injection simulation, the protrusion 116 provides a tactile feedback that injection simulation has completed. See FIG. 9A. The protrusion 116 also provides a visual feedback of completion of injection. FIG. 9A also shows a partial sectional view of the device 100 following completion of an injection simulation, wherein the rotating mechanism 126 is positioned toward the distal end of the device 100. As an alternative, or in addition to extension of the protrusion 116 through the aperture 112 in the outer housing 110, a visual feedback is also, or alternatively, provided by viewing a portion of the inner housing 114 through the indicator window 118 in the outer housing 110 of the device 110 as shown in FIG. 9B-9C. FIG. 9D shows an internal view of the protrusion 116, the first spring 130 and other structural features following completion of actuation. FIGS. 9B-9D are taken at cross-sectional line X-X of FIG. 9A.

Figure 10A:
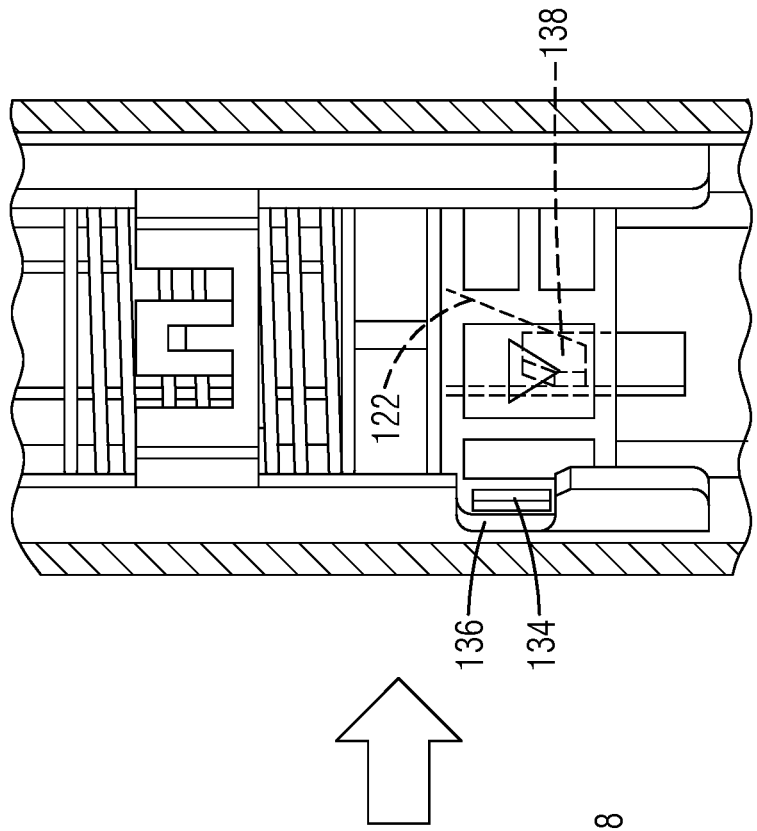
FIG. 10A is a partial sectional view of a resettable injection training device during reset.
Figure 10B:
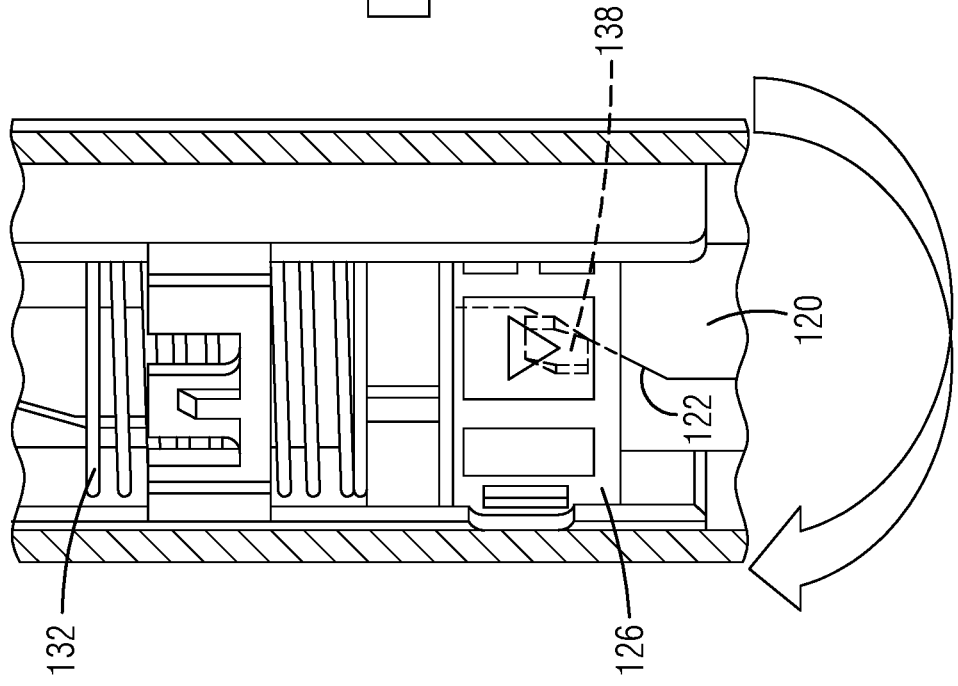
FIG. 10B is a partial sectional view of a resettable injection training device during reset.
Figure 10C:
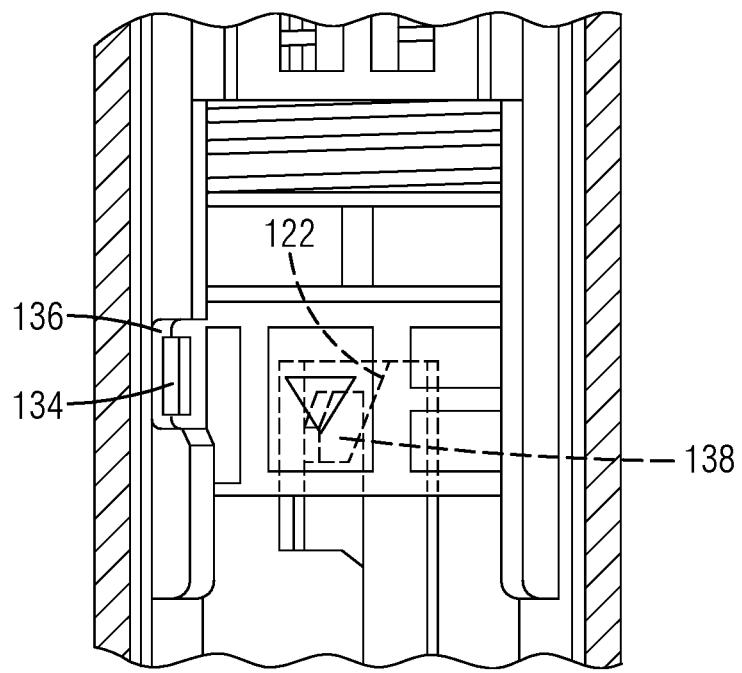
FIG. 10C is a partial sectional view of a resettable injection training device during reset.
Figure 10C:
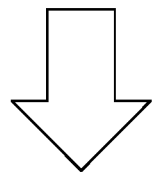
Figure 10D:
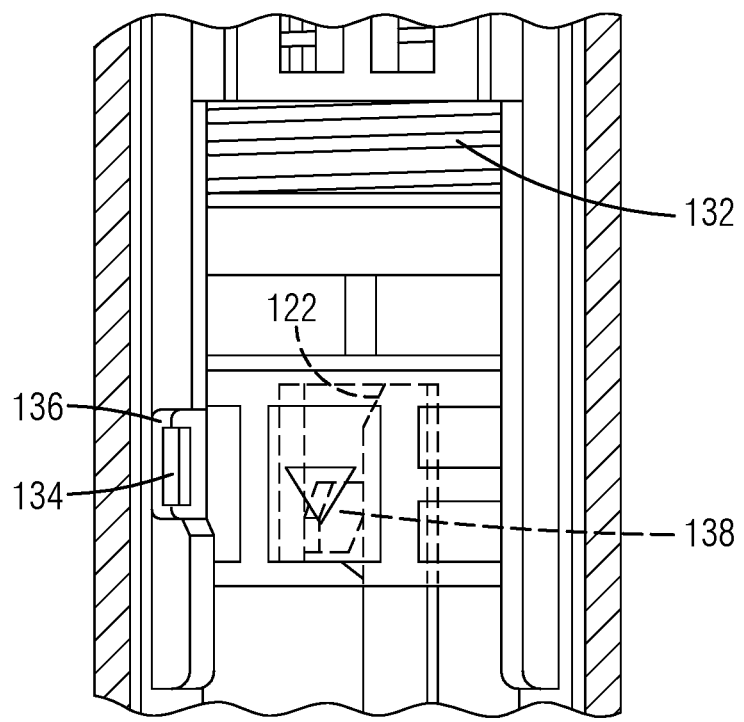
FIG. 10D is a partial sectional view of a resettable injection training device during reset.

Following actuation, the device is reset by way of the reset cap 128 shown in FIGS. 2A-2B by inserting the elongated rod 129 into the distal end of the device 100. Proximal movement of the cap 128 causes the plunger 120 to move proximally. By proximal movement of the plunger 120, the plunger ramp 122 interfaces with the inner tab 138 of the rotating mechanism 126, causing the rotating mechanism to move in a proximal direction and to rotate in the second direction as shown by the arrow in FIG. 10A. Movement of the rotating mechanism 126 continues in a proximal direction relative to the outer housing until the outer tab 134 interfaces with the inner housing groove 136. In one embodiment, due to the greater strength of the second spring 132 over the first spring 130, the interaction between the outer tab 134 and the groove 136 causes the inner housing 114 to be moved distally within the device by way of the second spring 132 until the inner housing 114 reaches its pre-simulation (reset) position. In the reset position, the protrusion 116 is retracted within the outer housing 110 and does not extend beyond the outer housing 110. Additionally, in the reset position of the device 100, the inner housing 114 is not visible via the indicator window 118 in the outer housing 110, and the device 100 is ready for a subsequent injection simulation. Prior to initiating a subsequent simulation, the reset cap 128 is removed from the device revealing the extended, unlocked safety shield.

Figure 11C:
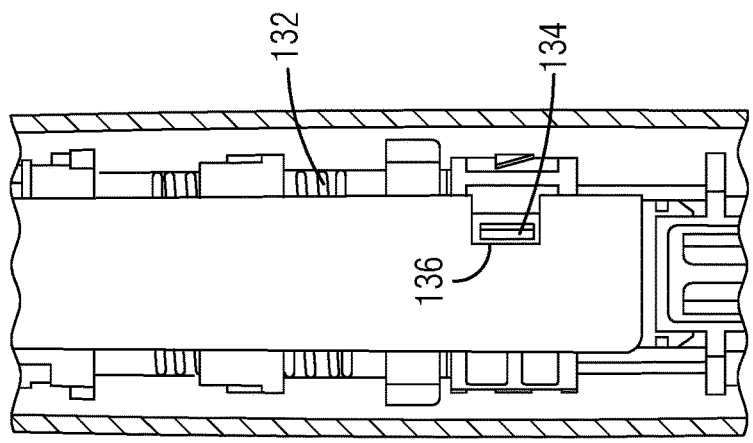
FIG. 11C is a partial sectional view of a resettable injection training device during reset.
Figure 11B:
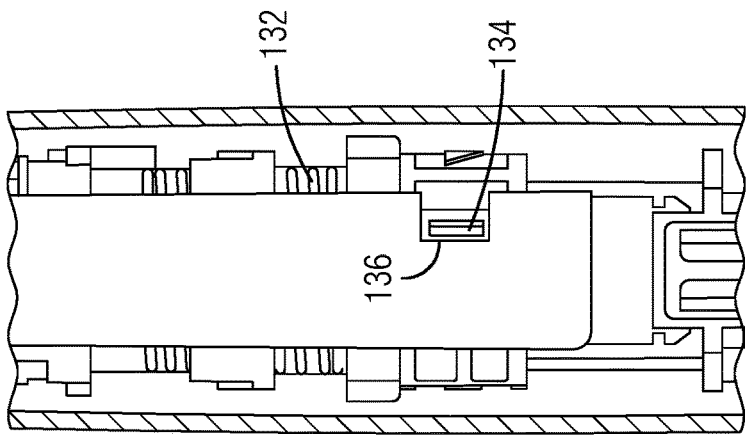
FIG. 11B is a partial sectional view of a resettable injection training device during reset.
Figure 11A:
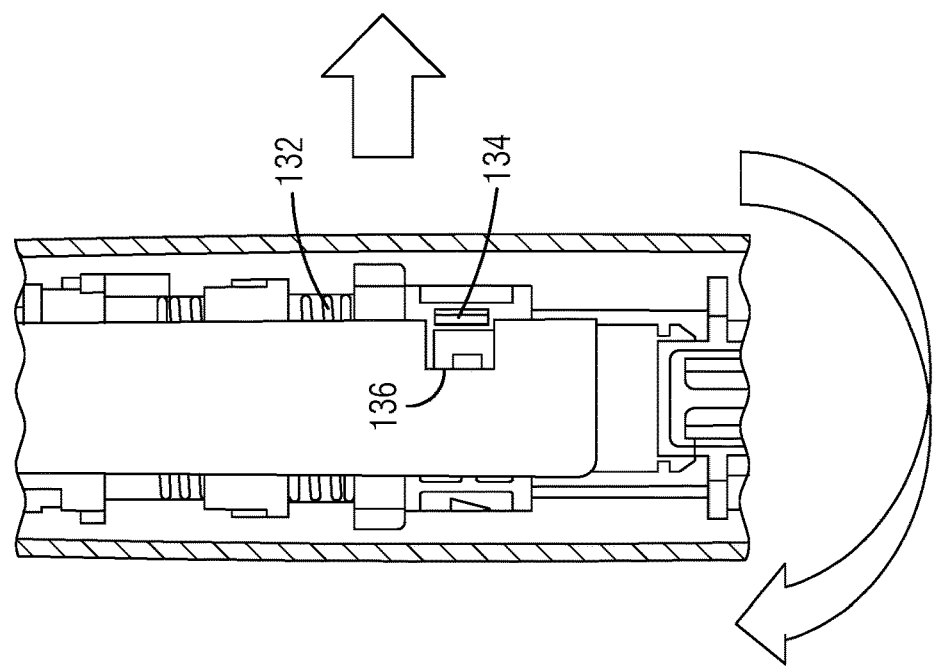
FIG. 11A is a partial sectional view of a resettable injection training device during reset.

FIGS. 11A-11C provide a view of the interaction between the inner housing groove 136 and the outer tab 134 of the rotating member during reset. FIG. 11A shows the rotating member prior to engaging with the groove 136. FIG. 11B shows the interface between the outer tab 134 and the groove 136 once the outer tab 134 has engaged the groove 136, and FIG. 11C demonstrates the distal movement of the inner housing 114 once the rotating member has engaged the inner housing as shown to reset the inner housing 114 to its distal position within the device 100.

In one embodiment, a method for providing a resettable injection training device including sensory feedback includes providing a resettable injection training device for simulating an injection, including an outer housing comprising a proximal end and a distal end, the proximal end comprising an aperture, an inner housing comprising a protrusion for extending through the aperture during use of the device, a first spring for interfacing with the inner housing, a plunger for moving relative to the inner housing from a proximal end to a distal end, said plunger comprising a ramped portion, a safety shield comprising a distal end for engaging with a target surface, said safety shield comprising a retracted position, an extended unlocked position and an extended locked position, a rotating member for interfacing with the inner housing, said rotating member comprising an inner tab and an outer tab, wherein said rotating member rotates in a first direction during actuation and in a second direction during reset, a second spring for interfacing with the rotating member, visual and/or tactile feedback; and a reset cap comprising an elongated rod for resetting the device from a post-actuation position to a pre-actuation position, wherein movement of the components relative to one another delivery the visual and/or tactile feedback to enhance the training experience.

In another embodiment a method for resetting a resettable injection training device comprising an outer housing, an inner housing, said inner housing moving relative to the outer housing during actuation and reset, a tactile feedback indicator and/or a visual feedback indicator, wherein actuation of the device delivers a tactile and/or visual feedback; and a reset cap for resetting the device to a reset position, such that the reset cap resets the tactile and or feedback indicator to a pre-use position, for a subsequent use comprises inserting at least a portion of the reset cap into the housing to reset the components of the housing to the pre-use position, including resetting the tactile feedback indicator and/or visual feedback indicator to its pre-use position. The benefits of a resettable device include the ability to reset all components of the device, including the mechanical components, to their pre-use position to allow for multiple subsequent trainings to reinforce the learning.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

What is claimed is:

1. A resettable injection training device for simulating an injection, comprising:
    an outer housing comprising a proximal end and a distal end, the proximal end comprising an aperture;
    an inner housing comprising a protrusion for extending through the aperture during use of the device;
    a first spring for interfacing with the inner housing,
    a plunger for moving relative to the inner housing from a proximal end to a distal end, said plunger comprising a ramped portion;
    a safety shield comprising a distal end for engaging with a target surface, said safety shield comprising a retracted position, an extended unlocked position and an extended locked position;
    a rotating member for interfacing with the inner housing, said rotating member comprising an inner tab and an outer tab, wherein said rotating member rotates in a first direction during actuation and in a second direction during reset;
    a second spring for interfacing with the rotating member;
    wherein the inner housing, outer housing, first or second spring, plunger, safety shield and/or rotating member provides visual or tactile feedback; and
    a reset cap comprising an elongated rod for resetting the device from a post-actuation position to a pre-actuation position.

2. The resettable injection training device of claim 1, wherein the outer housing comprises an indicator window for indicating a status of the device during an injection simulation.

3. The resettable injection training device of claim 1, wherein the outer tab of the rotating member interfaces with the inner housing to maintain the inner housing in a pre-actuation or reset position.

4. The resettable injection training device of claim 3, wherein the inner tab of the rotating member interfaces with the ramped portion of the plunger during actuation of the device to rotate the rotating member in the first direction to disengage the outer tab from the inner housing, releasing the inner housing to move in a proximal direction.

5. The resettable injection training device of claim 4, wherein the inner housing further comprises an inner housing groove for interfacing with the outer tab of the rotating member when the device is in the pre-actuation or reset position.

6. The resettable injection training device of claim 5, wherein disengagement of the rotating member from the inner housing causes the second spring to activate, moving the rotating member distally.

7. The resettable injection training device of claim 4, wherein distal movement of the plunger during actuation of the device releases the rotating member outer tab from the inner housing groove.

8. The resettable injection training device of claim 1, wherein the second spring comprises a compression spring.

9. The resettable injection training device of claim 1, wherein the first spring comprises a compression spring.

10. The resettable injection training device of claim 1, wherein a force on the safety shield moves the safety shield from an extended, unlocked position to a retracted position to actuate the device.

11. The resettable injection training device of claim 10, wherein movement of the safety shield to a retracted position releases the plunger, such that the plunger travels toward the distal end of the device.

12. The resettable injection training device of claim 1, wherein rotation of the rotating member in the first direction allows the first spring to advance the inner housing toward the proximal end.

13. The resettable injection training device of claim 1, wherein rotation of the rotating member in the first direction allows the second spring to advance the rotating member toward the distal end.

14. The resettable injection training device of claim 12, wherein the protrusion extends through the aperture providing visual and/or tactile feedback of completion of a simulation.

15. The resettable injection training device of claim 1, wherein during resetting the device, insertion of the reset cap into the distal end of the device causes the plunger to move proximally, causing proximal movement of the rotating member.

16. The resettable injection training device of claim 15, wherein during reset, an interface between the ramped portion of the plunger and the inner tab of the rotating member causes the rotating member to rotate in the second direction until the outer tab interfaces with the inner housing groove.

17. The resettable injection training device of claim 16, wherein the second spring causes the inner housing to move distally to reset the device by interface of the rotating member and the inner housing.

18. The resettable injection training device of claim 17, wherein the outer housing comprises an indicator window for indicating a status of the device during an injection simulation, wherein distal movement of the inner housing resets the indicator window for a subsequent use.

19. The resettable injection training device of claim 1, wherein the second spring comprises a greater force than the first spring.

20. The resettable injection training device of claim 1, wherein a force on the distal end of the safety shield causing movement of the safety shield from an extended unlocked position to a retracted position causes a first audible signal during actuation to indicate initiation of actuation.

21. The resettable injection training device of claim 1, wherein completion of distal plunger movement, rotation of the rotating member in the second direction, and proximal movement of the inner housing is accompanied by a second audible signal to indicate completion of an injection simulation.

* * * * *